US009566039B2

(12) United States Patent
Umekawa et al.

(10) Patent No.: US 9,566,039 B2
(45) Date of Patent: Feb. 14, 2017

(54) BED POSITIONING SYSTEM FOR RADIATION THERAPY

(71) Applicant: Hitachi, Ltd., Tokyo (JP)

(72) Inventors: Toru Umekawa, Tokyo (JP); Takamichi Aoki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 138 days.

(21) Appl. No.: 14/600,265

(22) Filed: Jan. 20, 2015

(65) Prior Publication Data

US 2015/0272530 A1 Oct. 1, 2015

(30) Foreign Application Priority Data

Mar. 27, 2014 (JP) ................. 2014-064970

(51) Int. Cl.
*A61B 6/03* (2006.01)
*A61B 6/00* (2006.01)
*A61B 6/04* (2006.01)
*A61N 5/10* (2006.01)

(52) U.S. Cl.
CPC .......... *A61B 6/5264* (2013.01); *A61B 6/035* (2013.01); *A61B 6/0407* (2013.01); *A61B 6/0457* (2013.01); *A61B 6/4035* (2013.01); *A61B 6/5217* (2013.01); *A61B 6/5247* (2013.01); *A61B 6/5258* (2013.01); *A61N 5/107* (2013.01); *A61N 5/1049* (2013.01); *A61B 6/032* (2013.01); *A61B 6/486* (2013.01); *A61N 2005/1061* (2013.01); *A61N 2005/1062* (2013.01)

(58) Field of Classification Search
CPC ....... A61B 6/032; A61B 6/035; A61B 6/0407; A61B 6/0457; A61B 6/4035; A61B 6/486; A61B 6/5217; A61B 6/5247; A61B 6/5258; A61B 6/5264; A61N 5/107; A61N 5/1049; A61N 2005/1061; A61N 2005/1062

See application file for complete search history.

(56) References Cited

U.S. PATENT DOCUMENTS

| | | | | |
|---|---|---|---|---|
| 2005/0053196 | A1* | 3/2005 | Mostafavi | A61B 6/4441 378/98.12 |
| 2005/0203373 | A1* | 9/2005 | Boese | A61B 6/481 600/407 |
| 2007/0133736 | A1* | 6/2007 | Chen | A61B 6/00 378/5 |
| 2008/0232664 | A1* | 9/2008 | Nagamine | A61N 5/1048 382/131 |

FOREIGN PATENT DOCUMENTS

JP 2006-149438 6/2006

* cited by examiner

*Primary Examiner* — David E Smith
(74) *Attorney, Agent, or Firm* — Mattingly & Malur, PC

(57) ABSTRACT

Provided is a bed positioning system for a radiation therapy system capable of capturing X-ray transparent images and CT images by rotating an X-ray tube and an X-ray detector around a subject on a bed, comprising: a transparent image registration system which generates a subtraction image from a first X-ray transparent image captured by the X-ray tube and the X-ray detector and a digitally reconstructed radiograph generated from a treatment plan CT image, corrects the first X-ray transparent image by use of a correction image generated by processing the subtraction image in a previously specified direction, and compares the first X-ray transparent image after the correction and the digitally reconstructed radiograph to determine a movement amount of the bed.

7 Claims, 4 Drawing Sheets

200 TRANSPARENT IMAGE
210 DIGITALLY RECONSTRUCTED RADIOGRAPH
220 SUBTRACTION IMAGE
230 CORRECTION IMAGE
240 CORRECTED TRANSPARENT IMAGE

BED POSITIONING SYSTEM FOR RADIATION THERAPY

BACKGROUND OF THE INVENTION

1. Field of the Invention

The present invention relates to a bed positioning system for radiation therapy.

2. Description of the Related Art

During radiation therapy, X-ray transparent images of the subject (patient) on a bed are captured and the bed is positioned according to the result of comparison between the captured images and a reference image in the treatment plan so that the position of the subject coincides with a planned position (position specified in the treatment plan).

In high-precision radiation therapy such as particle beam therapy and X-ray IMRT (Intensity Modulated Radiation Therapy), dose distribution concentrating at the target can be realized. Therefore, the positioning process is also required to position the target in the subject at the planned position with high accuracy.

For the positioning at the time of treatment (radiation therapy), an X-ray transparent image or an X-ray CT (Computed Tomography) image can be used. The X-ray transparent image is a two-dimensional image in which the positions of structures in high X-ray contrast (mainly, bone structure) can be clearly recognized and checked. The X-ray transparent image is shot in two directions orthogonal to each other and used for the positioning based on the bone structure, etc. in the subject. The X-ray CT image is a three-dimensional image in which soft tissues can also be recognized and checked. By use of the X-ray CT image, the position of the target of the radiation therapy is checked and the positioning of the subject is carried out. Since the two types of images are used selectively depending on the type of the treatment target in the subject and the method of the treatment, it is desirable that the two image capturing methods can be executed selectively in the same system.

The positioning is performed by using X-ray transparent images as follows. A digitally reconstructed radiograph (DRR) is generated from a treatment plan CT image by means of numerical simulation based on the relative positional relationship between the subject and the therapy system. An X-ray transparent image is previously captured at the position exactly according to the treatment plan. The digitally reconstructed radiograph (DRR) or the X-ray transparent image obtained is made to coincide with the subject position captured in the transparent image at the time of the treatment (2D/2D registration). Alternatively, digitally reconstructed radiographs (DRRs) according to various relative positional relationships between the subject and the therapy system are calculated from the treatment plan CT image and the positioning is carried out by calculating the deviation of the subject based on comparison with the transparent image at the time of the treatment (3D/2D registration).

In the positioning by use of a CT image, the cone-beam CT is mainly used. The radiation therapy system is generally equipped with a rotatable therapeutic radiation irradiation system for applying the therapeutic radiation to the subject (target) from any direction. By adding an X-ray image capturing system to the therapeutic radiation irradiation system, rotating image capturing is performed and the cone-beam CT image capturing function is implemented. A soft tissue position in the subject captured by the CT image capturing is made to coincide with the planned position, or the positioning is performed by using a bone structure or the like and whether the soft tissue position is at the correct position or not is checked. The X-ray image capturing system provided for the radiation therapy system is generally used also for the positioning by use of X-ray transparent images, enabling both types of positioning with a small number of devices.

A background technology for removing a structure other than the subject from a transparent image has been described in Japanese Patent No. 4344825. This patent literature describes a system for positioning a patient by using a digitally reconstructed radiograph (DRR) and an irradiation field confirmation image (LG: Linac Graphy), wherein the digitally reconstructed radiograph and the LG are registered with each other, the edge of a collimator in the LG is removed based on shape data of the collimator, and the deviation between the digitally reconstructed radiograph and the LG is detected by using the image obtained by the removal of the collimator edge.

SUMMARY OF THE INVENTION

In the cone-beam CT image capturing, there are cases where the image capturing is performed by attaching a bow-tie filter to the system in order to improve the image quality. As shown in FIG. 7, the bow-tie filter 6 is a metallic structure formed to reduce the amount of X-rays in the peripheral part where the thickness of the subject is small. The bow-tie filter 6 is arranged downstream of the X-ray tube. The thickness of the bow-tie filter 6 is uniform along the direction of the CT rotation axis but varies along a direction orthogonal to the rotation axis according to the thickness of the subject. Accordingly, in the X-ray transparent image captured by the bow-tie filter, the structure is captured in the peripheral part. In the reconstruction of a CT image, the reconstruction is performed in consideration of the structure captured in the CT image. On the other hand, an error can occur if an X-ray image in which the bow-tie filter has been captured is directly used for the 3D/2D registration. It is possible to detach the bow-tie filter from the image capturing system in order to accurately perform the 3D/2D registration. However, the detachment of the bow-tie filter takes a long time and that deteriorates the throughput of the treatment.

As a method for removing the bow-tie filter from the transparent image in which the bow-tie filter has been captured, it is possible to carry out the removal of the bow-tie filter based on previously loaded structure information on the bow-tie filter. However, in the actual transparent images, how the bow-tie filter is captured in the image varies depending on the conditions of the X-ray image capturing (e.g., X-ray intensity). When the structure that should be removed is the collimator, the removal is possible if only the projected shape of the collimator edge is known. However, when the structure that should be removed is the bow-tie filter, the bow-tie filter has been captured in the image while overlapping with the object (subject) of the image capturing. Therefore, the removal process has to be performed properly depending on how the bow-tie filter has been captured in the image. As described above, it is difficult to remove the bow-tie filter from the image by using the structure information alone. In reality, the removal process has to be carried out by using information on a plurality of bow-tie filter projection images captured in various X-ray image capturing conditions as the structure information and it is difficult to employ such a method for the actual radiation therapy.

It is therefore the primary object of the present invention to realize high-accuracy bed positioning by removing the bow-tie filter (which is necessary at the time of the CT image capturing) from images in the 3D/2D registration without the need of previously preparing image data for the removal.

In order to achieve the above object, an aspect of the present invention provides a bed positioning system for a radiation therapy system capable of capturing X-ray transparent images and CT images by rotating an X-ray tube and an X-ray detector around a subject on a bed, comprising: a transparent image registration system which generates a subtraction image from a first X-ray transparent image captured by the X-ray tube and the X-ray detector and a digitally reconstructed radiograph generated from a treatment plan CT image, corrects the first X-ray transparent image by use of a correction image generated by processing the subtraction image in a previously specified direction, and compares the first X-ray transparent image after the correction and the digitally reconstructed radiograph to determine a movement amount of the bed.

According to the present invention, high-accuracy bed positioning becomes possible by removing a structure such as the bow-tie filter from the CT image and the transparent images used for the positioning calculation without the need of previously preparing many pieces of correction image data.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

Figure 1:
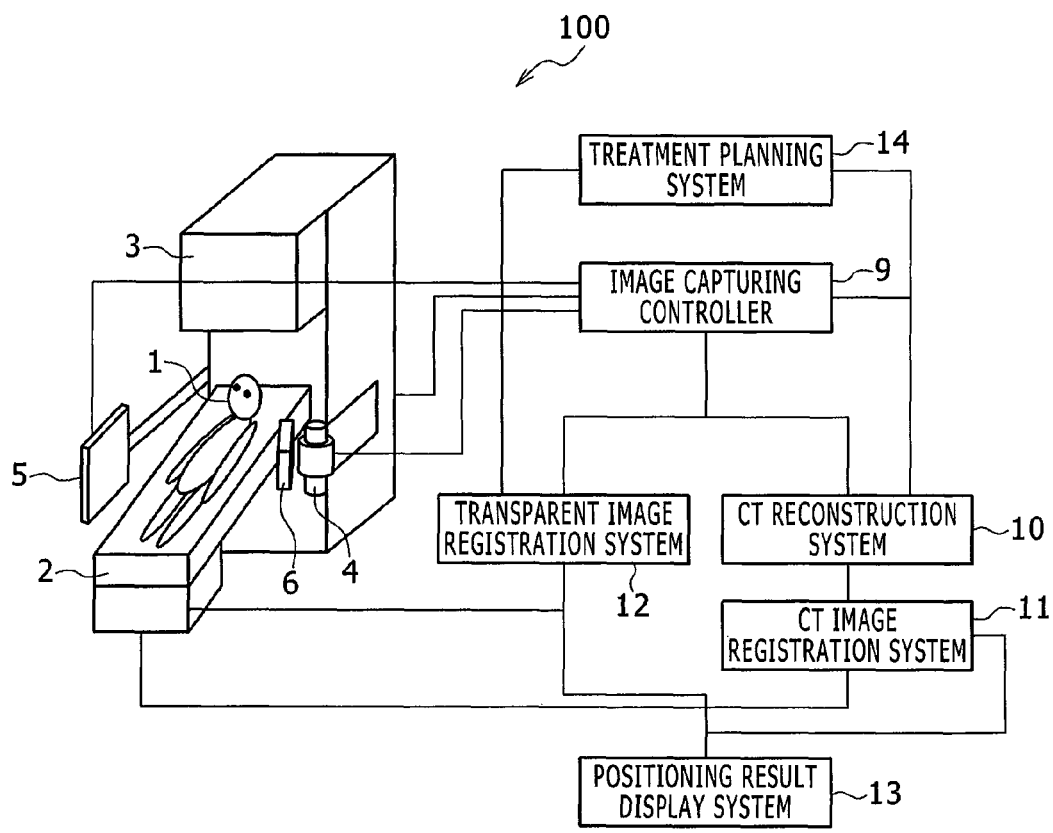
FIG. 1 is a schematic block diagram showing a treatment planning system and the configuration of a radiation therapy bed positioning system in accordance with an embodiment of the present invention.

Referring now to the drawings, a description will be given in detail of preferred embodiments of the present invention.

First Embodiment

A first embodiment of the present invention will be described below by taking a bed positioning system performing the 3D/2D registration as an example. FIG. 1 is a schematic block diagram showing an example of the configuration of a bed positioning system 100 in accordance with the first embodiment of the present invention. A subject 1 to receive the radiation therapy is supported on a bed (support table) 2. The bed 2 is equipped with a drive mechanism for parallel translation and rotation, and thus the bed 2 supporting the subject 1 can be moved by the drive mechanism. A therapeutic radiation irradiation system 3, having a rotation mechanism, is capable of applying the therapeutic radiation to the subject 1 from any direction (angle) around the rotation axis.

The therapeutic radiation irradiation system 3 is equipped with an X-ray tube 4 and an X-ray detector 5 via support arms. According to the rotation of the therapeutic radiation irradiation system 3, the X-ray tube 4 and the X-ray detector 5 rotate around the rotation axis. By rotating the X-ray tube 4 and the X-ray detector 5 around the subject 1 on the bed 2, a transparent image of the subject 1 from any direction can be captured.

At the time of the treatment (radiation therapy), an image capturing controller 9 rotates the therapeutic radiation irradiation system 3 to an image capturing angle by issuing commands thereto and then captures an X-ray image by controlling the X-ray tube 4 and the X-ray detector 5. The mode of the image capturing under the control of the image capturing controller 9 can be switched between an X-ray transparent image capturing mode (performing the image capturing while fixing the therapeutic radiation irradiation system 3 at a particular angle) and a CT image capturing mode (performing the image capturing in multiple directions while rotating the therapeutic radiation irradiation system 3).

Figure 7:
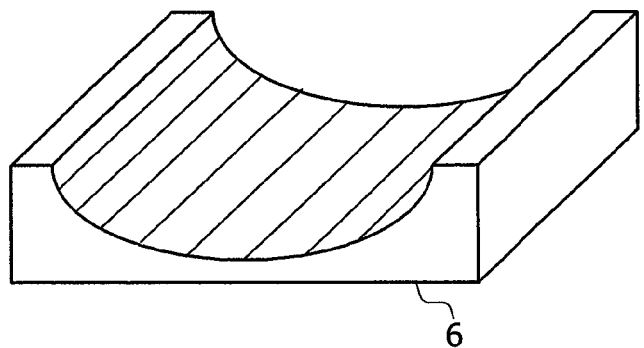
FIG. 7 is a schematic diagram showing a bow-tie filter.

In the CT image capturing mode of the image capturing controller 9, a plurality of transparent images of the subject 1 in multiple directions can be captured by shooting X-ray transparent images intermittently or continuously while rotating the X-ray tube 4 and the X-ray detector 5. A CT image of the subject 1 on the bed 2 can be acquired by reconstructing the captured images by use of a CT reconstruction system 10. The CT image includes a plurality of slice images of the subject 1. The plurality of slice images contain information on the three-dimensional structure of the subject 1. A bow-tie filter 6 may be arranged between the X-ray tube 4 and the X-ray detector 5 at the time of the CT image capturing, by which the image capturing of the subject 1 can be performed with high precision and the image quality of the CT image can be improved. The X-rays emitted from the X-ray tube 4 pass through the X-ray detector 5, thereafter pass through the subject 1, and are detected by the X-ray detector 5. As shown in FIG. 7, the bow-tie filter 6 is a metallic structure formed to reduce the amount of X-rays in the peripheral part where the thickness of the subject is small. The bow-tie filter 6 is arranged downstream of the X-ray tube 4. The thickness of the bow-tie filter 6 is uniform along the direction of the CT rotation axis but varies along a direction orthogonal to the rotation axis according to the thickness of the subject.

In the positioning by use of the CT image, the captured CT image is sent to a CT image registration system 11. The CT image registration system 11 calculates the positional deviation of the subject 1 from the treatment plan CT. In the calculation of the deviation, deviation from the treatment plan is determined by searching for a position where images look alike (image similarly is high) by using image similarity indices such as the mutual information and the correlation coefficients. A treatment time CT image (CT image at the time of the treatment) after compensating for the deviation and a treatment plan CT image are displayed on a positioning result display system 13. After confirmation by the operator, the CT image registration system 11 calculates the amount of movement (movement amount) of the bed 2 based on the determined deviation from the treatment plan and outputs the bed movement amount information to the therapeutic radiation irradiation system 3. The therapeutic radiation irradiation system 3 drives the bed 2 according to the received bed movement amount information and thereby moves the subject 1 to the correct position (planned position).

In the X-ray transparent image capturing mode of the image capturing controller 9, X-ray image capturing in directions used for the positioning is performed by use of the X-ray tube 4 and the X-ray detector 5. In general, X-ray image capturing in two directions, from the front and the side of the subject 1, is performed in the X-ray transparent image capturing mode. The captured images are sent to a transparent image registration system 12. The transparent image registration system 12 performs the 2D/2D registration calculation or the 3D/2D registration calculation. In the 2D/2D registration calculation, a digitally reconstructed radiograph (DRR) generated from a treatment plan CT image by means of numerical simulation based on the relative positional relationship between the subject 1 and the therapeutic radiation irradiation system 3 or an X-ray transparent image previously captured at the position exactly according to the treatment plan is made to coincide with the subject position captured in the transparent image at the time of the treatment. In the 3D/2D registration calculation, digitally reconstructed radiographs (DRRs) according to various relative positional relationships between the subject 1 and the therapeutic radiation irradiation system 3 are calculated from the treatment plan CT image and the registration is performed by calculating the deviation of the subject 1 based on comparison with the transparent image at the time of the treatment. Images after the compensation for the deviation (result of the calculation) are displayed on the display system 13. After confirmation by the operator, the transparent image registration system 12 calculates the movement amount of the bed 2 based on the determined deviation from the treatment plan and outputs the bed movement amount information to the therapeutic radiation irradiation system 3. The therapeutic radiation irradiation system 3 drives the bed 2 according to the received bed movement amount information and thereby moves the subject 1 to the correct position.

Figure 2:
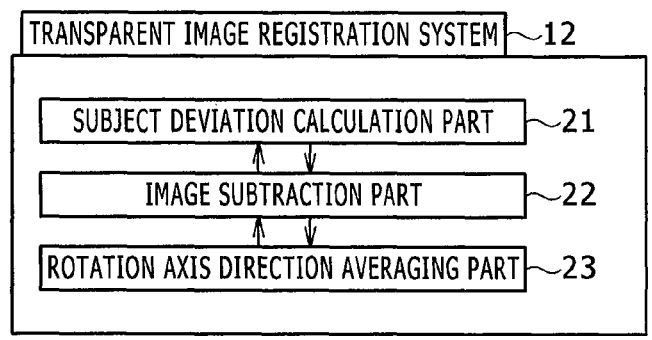
FIG. 2 is a block diagram showing an example of the configuration of a transparent image registration system as a component of a radiation therapy bed positioning system in a first embodiment of the present invention.

FIG. 2 is a block diagram showing an example of the configuration of the transparent image registration system 12. The transparent image registration system 12 includes a subject deviation calculation part 21, an image subtraction part 22, and a rotation axis direction averaging part 23. The subject deviation calculation part 21 performs the 3D/2D registration calculation. The image subtraction part 22 generates a digitally reconstructed radiograph (DRR) at a position coinciding with the X-ray transparent image based on the determined deviation and subtracts the digitally reconstructed radiograph from the X-ray transparent image. The rotation axis direction averaging part 23 averages an image in a CT image capturing axis direction.

Figure 3:
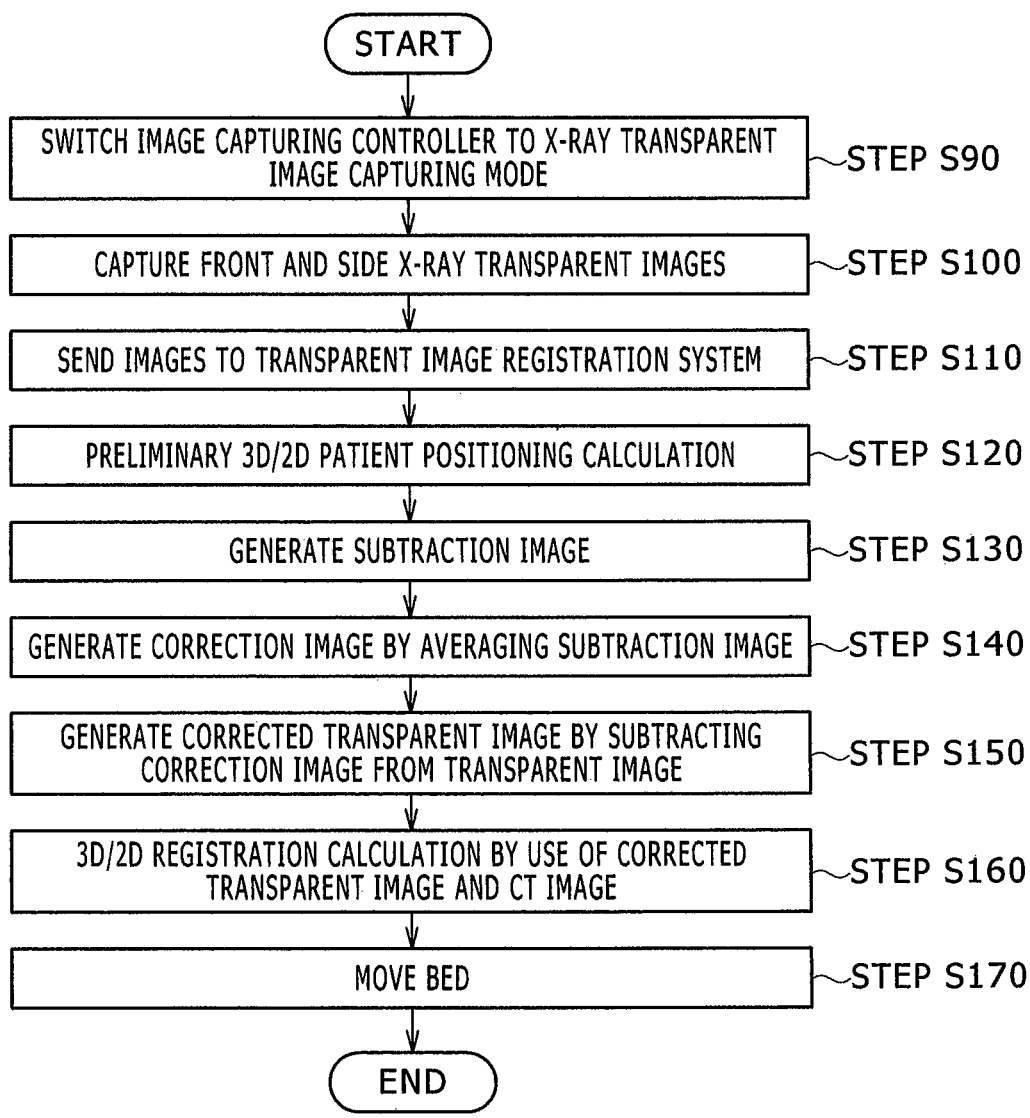
FIG. 3 is a flow chart showing the flow of the bed positioning performed by the radiation therapy bed positioning system in the first embodiment.
Figure 4:
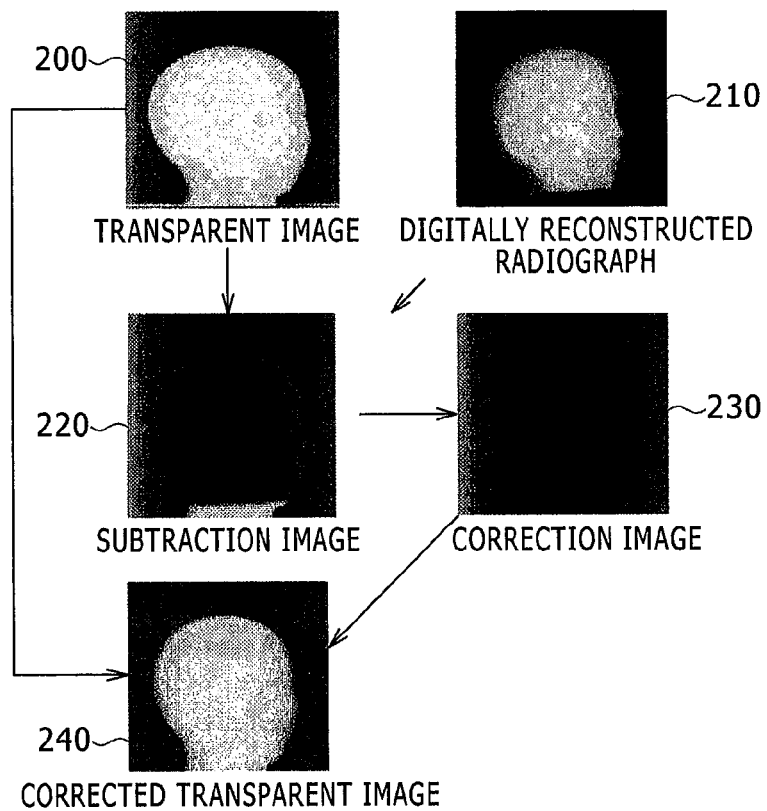
FIG. 4 is an explanatory drawing for explaining a procedure for generating a corrected transparent image from a transparent image.

Next, a process executed in this embodiment will be explained below referring to FIGS. 3 and 4. FIG. 3 is a flow chart showing the flow of the process executed in this embodiment. FIG. 4 is an explanatory drawing for explaining a procedure for generating a corrected transparent image from a transparent image.

When the bed positioning by the bed positioning system 100 is started, the mode of the image capturing controller 9 is switched to the X-ray transparent image capturing mode according to a command from the operator (step S90).

Thereafter, the process advances to step S100, in which X-ray transparent images 200 in the two directions (from the front and the side of the subject 1) are captured. In cases where the therapeutic radiation irradiation system 3 has only one pair of X-ray tube 4 and X-ray detector 5, the image capturing in each direction is carried out after rotating the therapeutic radiation irradiation system 3 (rotating the X-ray tube 4 and the X-ray detector 5) and stopping the X-ray tube 4 and the X-ray detector 5 at prescribed positions. In cases where the therapeutic radiation irradiation system 3 has multiple pairs of X-ray tube 4 and X-ray detector 5, the image capturing in multiple directions may be carried out substantially at the same time.

Thereafter, the process advances to step S110, in which the image capturing controller 9 sends the X-ray transparent images 200 in the two directions to the transparent image registration system 12.

Thereafter, the process advances to step S120, in which the subject deviation calculation part 21 of the transparent image registration system 12 preliminarily performs the 3D/2D registration calculation based on the X-ray transparent images 200 in the two directions and the CT image. At this stage, the bow-tie filter 6 has also been captured in the X-ray transparent images 200 and an error has occurred since the comparison of the image similarity is made in the entire image containing structures other than the subject 1. However, the projection image of the subject 1 in each digitally reconstructed radiograph 210 substantially coincides with the projection image of the subject 1 in each X-ray transparent image 200. Since the bow-tie filter 6 has not been captured in each digitally reconstructed radiograph 210 generated from the treatment plan CT image used as the reference image, the coincidence between the digitally reconstructed radiograph 210 and the X-ray transparent image 200 has occurred only in the projection image of the subject 1 and the other structures have been captured only in the X-ray transparent image 200.

Thereafter, the process advances to step S130, in which the image subtraction part 22 generates a subtraction image 220 from each X-ray transparent image 200 by subtracting the digitally reconstructed radiograph 210 in the preliminarily registered arrangement from the X-ray transparent image 200. Since the projection image of the subject 1 in the digitally reconstructed radiograph 210 and that in the X-ray transparent image 200 substantially coincide with each other, the subtraction image 220 is generated as an image containing almost only the structures other than the subject 1. Especially when the bow-tie filter 6 is in, bow-tie filter components (components corresponding to the bow-tie filter 6) are densely captured in the image. The subtraction for generating the subtraction image 220 may also be performed while multiplying an image by a preset coefficient. Further image processing such as a bone emphasizing process may also be conducted. The generation of the digitally reconstructed radiograph 210 may also be performed after previously removing the bed (which is easy to separate) from the CT image.

Thereafter, the process advances to step S140, in which the rotation axis direction averaging part 23 averages each subtraction image 220 in the CT image capturing axis direction (i.e., the direction of the rotation axis of the X-ray tube 4 and the X-ray detector 5 of the therapeutic radiation irradiation system 3). This averaging is performed since the thickness of the bow-tie filter 6 is substantially uniform along the CT image capturing axis direction. Although materials other than the bow-tie filter 6 also exist in the subtraction image 220, only a medium that is uniform along the CT image capturing axis direction is emphasized as the result of the averaging by the averaging process. The averaged image will hereinafter be referred to as a "correction image 230".

In cases where images in multiple angles (multiple directions) are captured by a pair of X-ray tube 4 and X-ray detector 5, the capturing of the multiple images is performed by using the same bow-tie filter 6. In this case, the bow-tie filter components in the correction images 230 should become identical with each other. Therefore, it is also possible to reduce the error by taking the average of the correction images 230 acquired in the multiple directions by the rotation axis direction averaging part 23.

Thereafter, the process advances to step S150, in which the image subtraction part 22 generates a corrected transparent image (second X-ray transparent image) 240 from each transparent image 200 by subtracting the correction image 230 from the transparent image 200. The corrected transparent images 240 are generated as images in which the bow-tie filter components have been reduced and almost only the subject 1 has been captured.

Thereafter, the process advances to step S160, in which the subject deviation calculation part 21 performs the 3D/2D registration calculation by using the corrected transparent images 240 and the CT image. Since both the corrected transparent images 240 and the digitally reconstructed radiographs 210 are images containing almost only the subject 1, positioning with high accuracy becomes possible.

Thereafter, the process advances to step S170, in which the bed 2 is moved by sending information on the bed position (compensating for the positional deviation) from the transparent image registration system 12 to the bed 2.

Incidentally, positioning calculation with still higher accuracy becomes possible by correcting the generation of the corrected transparent images 240 (step S130-step S150) based on the result of the high-accuracy positioning calculation obtained in the step S160. It is also possible to further increase the accuracy of the positioning calculation by carrying out this process recursively.

Second Embodiment

Figure 5:
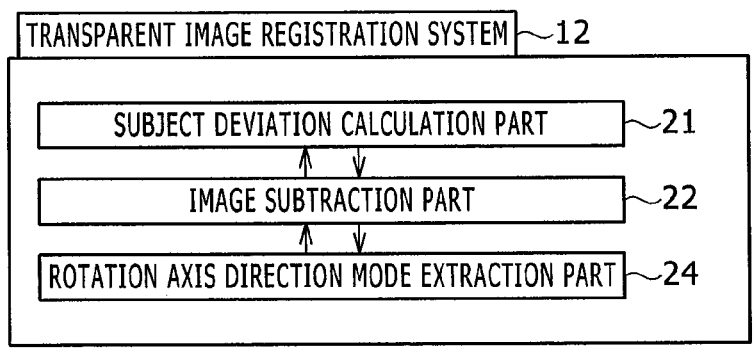
FIG. 5 is a block diagram showing an example of the configuration of a transparent image registration system as a component of a radiation therapy bed positioning system in a second embodiment of the present invention.

A second embodiment of the present invention will be described below. In this embodiment, the rotation axis direction averaging part 23 in the transparent image registration system 12 for executing the 3D/2D registration in the bed positioning system 100 described in the first embodiment is replaced with a rotation axis direction mode extraction part 24 shown in FIG. 5.

Figure 6:
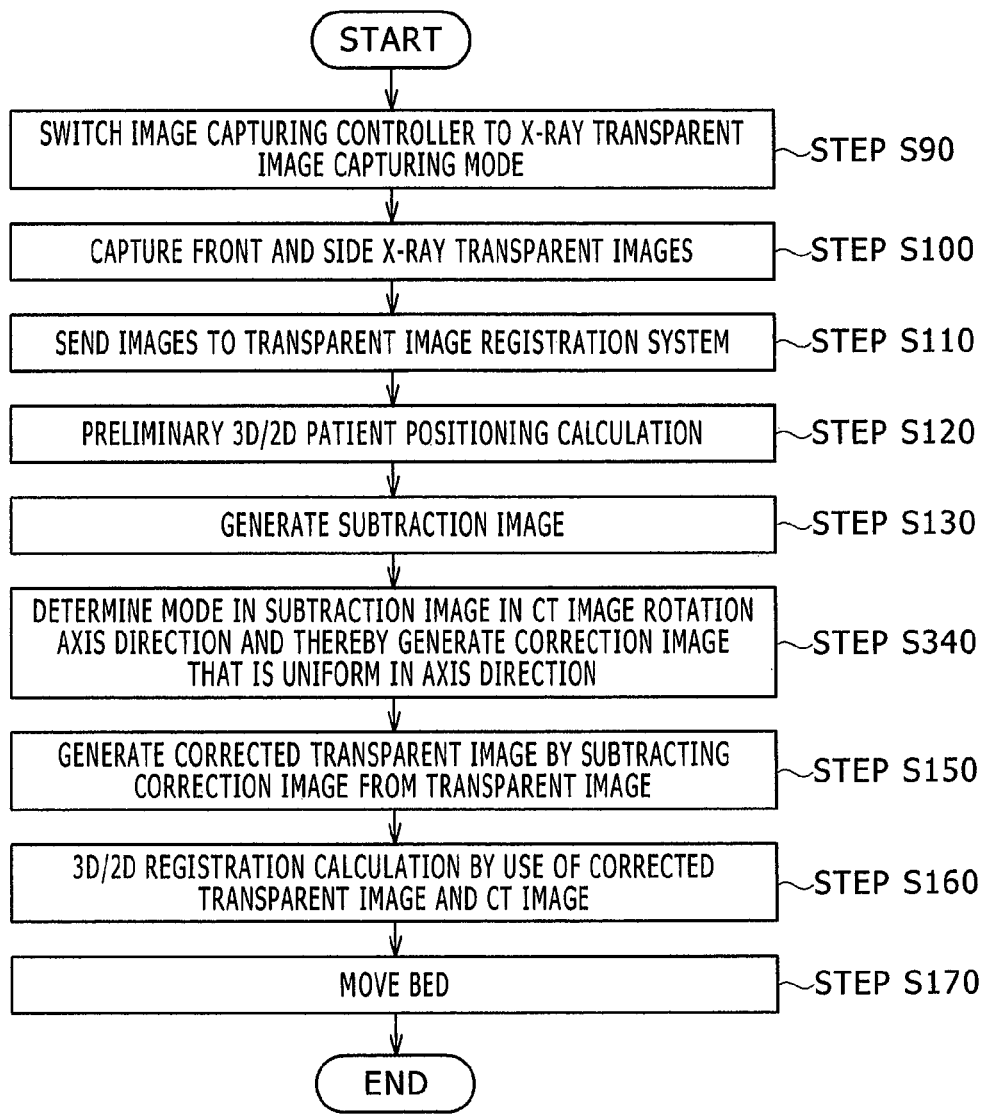
FIG. 6 is a flow chart showing the flow of the bed positioning performed by the radiation therapy bed positioning system in the second embodiment.

FIG. 6 is a flow chart showing the flow of a process executed in this embodiment. In FIG. 6, the step S140 in the flow chart of FIG. 3 is replaced with step S340. The process up to the generation of the subtraction images 220 is executed in the same flow as in the flow chart of the first embodiment (FIG. 3). In the step S340, the mode is determined instead of taking the average in the CT image rotation axis direction. The "mode" is determined as follows: Pixels in the image on a line in the CT image capturing axis direction are divided (classified) into pixel groups each having the same pixel value. The "mode" is determined as the pixel value of the pixel group having the largest number of pixels. The use of the mode is effective especially when the subject 1 has been only partially captured in the entire image. In such cases, there exists an area that has been imaged by the passage of the X-rays through the bow-tie filter 6 alone. Such an area is uniform. In contrast, an area imaged by the passage of the X-rays through the subject 1 has been formed an image of the bow-tie filter 6 alone due to the subtraction process. By determining the mode in this image in the CT image rotation axis direction, the area in which only the bow-tie filter 6 has been captured is extracted. Therefore, high-accuracy positioning calculation (registration calculation) removing the bow-tie filter with higher accuracy becomes possible by using an image having a uniform value equal to the mode determined in the CT image rotation axis direction as the correction image 230.

What is claimed is:

1. A bed positioning system for a radiation therapy system capable of capturing X-ray transparent images and CT images by rotating an X-ray tube and an X-ray detector around a subject on a bed, comprising:
   a transparent image registration system which generates a subtraction image from a first X-ray transparent image captured by the X-ray tube and the X-ray detector and a digitally reconstructed radiograph generated from a treatment plan CT image, corrects the first X-ray transparent image by use of a correction image generated by processing the subtraction image in a previously specified direction, and compares the first X-ray transparent image after the correction and the digitally reconstructed radiograph to determine a movement amount of the bed.

2. The bed positioning system according to claim 1, wherein the transparent image registration system generates the correction image by averaging the subtraction image in a previously specified direction or by determining the mode of the subtraction image in the specified direction.

3. The bed positioning system according to claim 1, comprising a structure which can be arranged between the X-ray tube and the X-ray detector, wherein:
   the first X-ray transparent image is a transparent image that has been captured by arranging the structure between the X-ray tube and the X-ray detector, and
   the treatment plan CT image is a reference CT image in which the structure has not been captured.

4. The bed positioning system according to claim 3, wherein the structure is configured so that its thickness is substantially uniform along a direction of a rotation axis of the X-ray tube and the X-ray detector but varies along a direction orthogonal to the rotation axis.

5. The bed positioning system according to claim 3, wherein the transparent image registration system generates a second X-ray transparent image, as an image obtained by removing the structure from the first X-ray transparent image, by correcting the first X-ray transparent image by use of the correction image.

6. The bed positioning system according to claim 2, comprising a structure which can be arranged between the X-ray tube and the X-ray detector, wherein:
   the first X-ray transparent image is a transparent image that has been captured by arranging the structure between the X-ray tube and the X-ray detector, and
   the treatment plan CT image is a reference CT image in which the structure has not been captured.

7. The bed positioning system according to claim 4, wherein the transparent image registration system generates a second X-ray transparent image, as an image obtained by removing the structure from the first X-ray transparent image, by correcting the first X-ray transparent image by use of the correction image.

* * * * *